United States Patent [19]

Nisato et al.

[11] Patent Number: 4,474,790
[45] Date of Patent: Oct. 2, 1984

[54] THIOALKYLAMIDE OF NICOTINIC ACID 1-OXIDE, ITS SALTS, AND PHARMACEUTICAL COMPOSITIONS

[75] Inventors: Dino Nisato, Pavia; Sergio Boveri, Tortona, both of Italy

[73] Assignee: SANOFI, Paris, France

[21] Appl. No.: 354,519

[22] Filed: Mar. 3, 1982

[30] Foreign Application Priority Data

Mar. 11, 1981 [FR] France .................. 81 04892

[51] Int. Cl.³ .................. A61K 31/455; C07D 405/12
[52] U.S. Cl. ..................................... 424/266; 546/283
[58] Field of Search ........................ 546/283; 424/266

[56] References Cited

U.S. PATENT DOCUMENTS 4,318,858   3/1982   Hirai et al. .................. 260/347.2

OTHER PUBLICATIONS

Bickel, Pharmacological Reviews, vol. 21, No. 4, pp. 325-355, Williams & Wilkins Co., Publishers, (Dec. 1969).

Burgers Medicinal Chemistry, Fourth Edition, Part III, pp. 537-540, Wiley-Interscience, Publishers, RS 403 B8, (1979).

*Primary Examiner*—Alan L. Rotman

*Attorney, Agent, or Firm*—Weingarten, Schurgin, Gagnebin & Hayes

[57] ABSTRACT

The invention relates to thioalkylamide of nicotinic acid 1-oxide with $H_2$ receptor blocking activity, of formula:

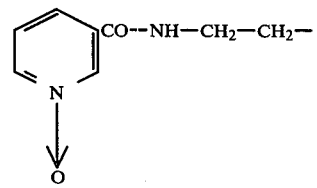

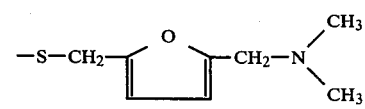

and to its pharmaceutically acceptable salts, to a process for preparing same by reaction of 2-(5-dimethylaminomethylfuran-2-ylmethylthio)ethylamine with a functional derivative of nicotinic acid 1-oxide and possible salification, and to pharmaceutical compositions containing same.

4 Claims, No Drawings

THIOALKYLAMIDE OF NICOTINIC ACID 1-OXIDE, ITS SALTS, AND PHARMACEUTICAL COMPOSITIONS

The present invention relates to a novel thioalkylamide having a histamine $H_2$ receptor blocking activity, to its salts, to a process for preparation thereof and to pharmaceutical compositions containing same as active ingredients.

After the subdivision of histamine receptors into $H_1$ receptors (Ash and Schild, Brit.J.Pharmac.Chemother. 1966, 27, 427) and $H_2$ receptors (Black et al., Nature 1972, 236, 385) and the discovery that the selective block of the $H_2$ receptors provokes an inhibition of the gastric secretion, numerous products have been proposed as antagonists of the histamine $H_2$ receptors, hereinafter indicated "$H_2$ blockers". The compounds having received the International Non-proprietary Names burimamide, metiamide, cimetidine, ranitidine, tiotidine, etintidine, oxmetidine have thus formed the subject matter of a large number of scientific publications and one of them, cimetidine, already constitutes a tool in the doctor's hand for the treatment of ulcerous disease.

All the above products are characterised by the presence in their molecule of the following structure:

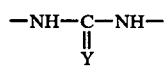   I where Y represents an atom of oxygen or of sulfur, or a group N—CN or CH—NO$_2$, said structure being linear or included in a cycle as in the case of oxmetidine. The above products are therefore all characterised by the presence of two geminal atoms of nitrogen with respect to one atom of carbon.

It is also known that histamine $H_2$ receptors are located not only in the gastric mucous membrane but also in the sinusal node, in the ventricular myocardium and in the coronary vessels and that the known $H_2$ blockers are active both on the cardiac and gastric receptors. In this way, the block of the cardiac $H_2$ receptors may be the cause of bradycardia and of asystolia observed as secondary effects in the treatment of ulcerous disease by cimetidine (Clinica Terapeutica, 1981, 96, 81-91, in particular page 84).

It is therefore desirable to have available compounds which present a dissociation between the gastric and cardiac $H_2$ receptor blocking activity, in favour of the former, which are further capable of giving fewer side effects at cardiac level.

It has now been found that a nicotinamide 1-oxide not presenting structure I hereinabove has a good action antagonising the histamine $H_2$ receptors and that this action is preferably produced at gastric $H_2$ receptor level.

Thus, according to one of its aspects, the present invention provides a novel thioalkylamide characterised by the following formula:

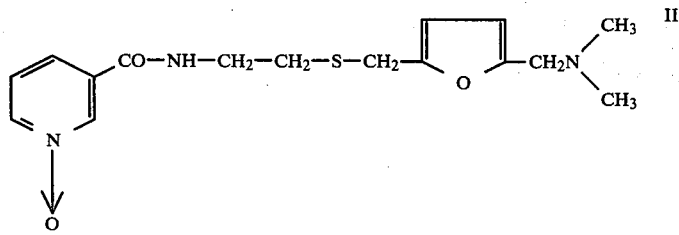   II as well as its pharmaceutically acceptable salts.

The pharmaceutically acceptable salts include the non-toxic salts derived from mineral or organic acids salifying one or the two basic functions present in the molecule of the compound of formula II, such as hydrochloride, hydrobromide, sulfate, succinate, tartrate, citrate, fumarate, maleate, 4,4'-methylene-bis-(3-hydroxy-2naphthoate), hereinafter designated "pamoate", 2-naphthalene-sulfonate, hereinafter designated "napsylate", methanesulfonate, hereinafter designated "mesylate", p-toluenesulfonate, hereinafter designated "tosylate", and the like.

According to another of its aspects, the present invention relates to a process for preparing the novel compound of formula II hereinabove, said process being characterised in that the 2-(5-dimethylaminomethylfuran-2-ylmethylthio)-ethylamine of formula

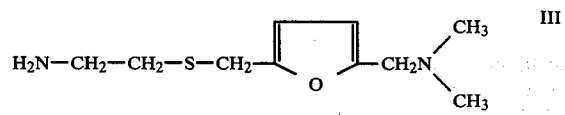   III is treated with a functional derivative of the nicotinic acid 1-oxide in an organic solvent at a temperature between 0° C. and the boiling temperature of the solvent employed.

Anhydride, a mixed anhydride, chloride or an activated ester may be used as suitable functional derivative.

The temperature of reaction may vary between 0° C. and the boiling point of the solvent employed, but operation is generally carried out at room temperature. It may be preferable to conduct the reaction in the cold when it is exothermic, as in the case of chloride being used as functional derivative of the nicotinic acid 1-oxide.

An alcohol, such as methanol or ethanol, or a halogenated solvent, such as methylene chloride, dichloroethane, chloroform and the like is preferably used as a reaction solvent, but other organic solvents compatible with the reagents employed, for example dioxan, tetrahydrofuran or a hydrocarbon such as hexane may also be used.

The reaction may be carried out in the presence of a proton acceptor, for example an alkaline carbonate or a tertiary amine, in the case of hydrochloric acid, or another acid, being released during the reaction, but this proton acceptor is not critical for obtaining the final product.

The reaction is fairly rapid; after 2-4 hours at room temperature, the reaction is generally over and the thioalkylamide of formula II obtained is isolated according to conventional techniques in the form of free base or one of its salts.

The free base may be converted into one of its pharmaceutically acceptable salts by treatment with a solution of the suitable acid in an organic solvent and the salt thus obtained is isolated according to conventional techniques, generally by simple filtration of the precipitate.

If, at the end of the reaction, the thioalkylamide of formula II is isolated in the form of salt, the corresponding free base may be prepared by liberating it with a alkaline hydroxide carbonate.

The novel compound of formula II of the present invention, as well as its pharmaceutically acceptable salts, act as selective antagonists of the histamine $H_2$ receptors by selectively inhibiting the gastric secretion at gastric $H_2$ receptor level with slight activity on the cardiac $H_2$ receptors and are therefore useful for the treatment of ulcer disease.

The selectivity of the activity of the product of the present invention towards the receptors of type $H_2$ is confirmed by the absence of anticholinergic and papaverine-like activity of type $H_1$, in the test of the contraction induced by histamine on the isolated guinea pig ileum.

The antagonistic activity of the compounds of the present invention at gastric histamine $H_2$ receptor level has been assessed in the test of the inhibition of the secretion induced by histamine on the isolated stomach mucous membrane of the Guinea pig (P. Holton and J. Spencer, J.Physiol.1976, 255; 465–479).

The antagonistic activity of the compounds of the present invention at cardiac histamine $H_2$ receptor level has been assessed in the test of the inhibition of the histamine-induced frequency increase in the guinea pig right atrium (D. Rheinhardt et al, Agents and Actions 1974, 4;127–221).

Table I shows, for the compound of the invention, in the form of dihydrochloride, indicated in the examples below by its code number CM 57755 and for two reference products 2-cyano-1-methyl-3-[2[(5-methylimidazol-4-yl)methylthio]ethyl]guanidine, hereinafter designated by its International Non-proprietary Name "cimetidine" and N-[2[[5-](dimethylamino)methyl]furfuryl]thio]ethyl]-N'-methyl-2-nitro-1,1-ethenediamine, hereinafter designated by its International Non-proprietary Name "ranitidine", described in Patent Application FR 2 360 587;

the concentration of product under examination which inhibits by 50% the increase in the frequency induced by histamine on the isolated right atrium of the Guinea pig ($IC_{50o}$)

the concentration of product under examination which inhibits by 50% the secretion induced by histamine on the isolated stomach mucous membrane of the Guinea pig ($IC_{50m}$)

the ratio $IC_{50m}/IC_{50o}$.

TABLE I

| Compound | $IC_{50o}$ (M. $10^{-6}$) | $IC_{50m}$ (M. $10^{-6}$) | $IC_{50m}/IC_{50o}$ |
|---|---|---|---|
| cimetidine | 0.4 | 6.6 | 16.5 |
| ranitidine | 0.086 | 0.65 | 7.6 |
| CM 57755 | 4.3 | 9.2 | 2.13 |

The very low value of the $IC_{50m}/IC_{50o}$ ratio relative to the compound of the present invention, much lower than that of the reference compounds, shows that the CM 57755 is capable of antagonising gastric hypersecretion more selectively than the positive chronotropic action provoked by histamine; namely, it shows a greater affinity for the gastric $H_2$ receptors than for the cardiac $H_2$ receptors.

The antagonistic activity of the products of the present invention towards the gastric histamine $H_2$ receptors was confirmed in the test of the antisecretory activity based on the antagonism to the hypersecretion provoked by histamine in the rat according to the method of Ghosh and Schild (Brit. J. Pharmacol.1958; 13, 54). According to this test, a gastric acid hypersecretion is induced by intravenous infusion of a submaximal dose equivalent to 15 mcmol/kg/hour and the gastric secretion is measured by perfusion of a physiological solution at a constant speed in the stomach of the animal. Under these conditions, the CM 57755 inhibits the 50% by hypersecretion at the dose of 0.9 mg/kg by the intravenous route; the $LD_{50}$ of the product by the intravenous route in the rat is 300 mg/kg.

The antisecretory activity of the products of the present invention was assessed in the cat having a gastric fistula according to the method of Emas et al.(Gastroenterology, 1969; 39, 771) using, as hypersecretor, dimaprit at the dose of 640 mcg/kg/hour. Under these conditions, the CM 57755, administered by venous perfusion as well as by intragastric route, antagonises in dose-dependent manner the hypersecretion provoked by the dimaprit. It activity is comparable, on molar basis, to that of the cimetidine used as reference compound. The product of the present invention shows, however, a long duration of action after the suspension of the treatment, whilst the effect of the reference product is more transient.

With respect to their degree of activity, the compounds of the present invention are little toxic and present a good therapeutic index.

According to another of its aspects, the present invention relates to pharmaceutical compositions containing, as active ingredients, the thioalkylamide of nicotinic acid 1-oxide of formula II hereinabove, as well as its pharmaceutically acceptable addition salts.

In the pharmaceutical compositions with $H_2$ receptor blocking activity according to the present invention, for oral, sublingual, sub-cutaneous, intramuscular, intravenous, transdermic or rectal administration, the active ingredients can be administered in unit forms of administration, with conventional pharmaceutical supports, to animals and to human beings in the treatment of gastric hypersecretion and peptic ulcers.

Among the appropriate unit forms of administration, there are the forms of administration by the oral route such as tablets, capsules, powders, granules and oral solutions and suspensions and the forms of sublingual administration, as well as the forms of parenteral administration useful for sub-cutaneous, intramuscular or intravenous administration.

In order to obtain the desired $H_2$ receptor blocking effect, the dose of active ingredient may vary between 1 and 100 mg per kg of body weight and per day, preferably from 10 to 50 mg per kg and per day.

Each unit dose may contain from 10 to 1000 mg of active ingredient in combination with a pharmaceutical carrier. This unit dose may be administered 1 to 4 times per day.

When a solid composition is prepared in the form of tablets, the main active ingredient is mixed with a pharmaceutical excipient such as gelatine, starch, lactose, magnesium stearate, talc, arabic gum or the like. The tablets may be coated with saccharose or other appropriate materials or they may be treated so that their activity is extended or delayed and that they continually release a predetermined quantity of active ingredient.

A preparation in capsules is obtained by mixing the active ingredient with a diluent and by pouring the mixture obtained in soft or hard capsules.

A preparation in the form of syrup or elixir may contain the active ingredient jointly with a possibly acaloric sweetening agent, methylparaben and propylparaben as antiseptics, as well as a flavouring and an appropriate dye.

Water-dispersible powders or granulates may contain the active ingredient mixed with dispersing agents or wetting agents, or suspending agents such as polyvinylpirrolidone and the like, and with sweetening agents or taste correctors.

For rectal application, suppositories are prepared with binding agents melting at rectal temperature, for example cocoa butter or polyethyleneglycols.

For parenteral administration, aqueous suspensions, isotonic saline solutions or sterile injectable solutions are used, which contain pharmacologically compatible dispersing and/or wetting agents, for example propyleneglycol or butylene glycol.

The active ingredient may also be formulated in the form of microcapsules, possibly with one or more supports or additives.

The following examples illustrate the invention without, however, limiting its scope.

EXAMPLE 1

Nine nicotinoyl chloride 1-oxide hydrochloride are added, in portions, with stirring and at the temperature of 0° to 5° C., to a solution of 8.6 g of 2-(5-dimethylalminomethylfuran-2ylmethylthio)ethylamine and 12.2 g of 4-dimethylaminopyridine in 80 ml of methylene chloride. The mixture is stirred for 30 minutes at 0°–5° C. and for 30 minutes at room temperature, then is filtered and the solvent is evaporated under reduced pressure. The residue is taken up in 80 ml of isopropanol and is acidified with hydrochloric acid in isopropanol. The solution cooled with ice water and, 30 minutes after, is filtered. 15.5 g of N-[2-(5-dimethylaminomethylfuran-2-ylmethylthio)ethyl]-3-pyridinecarboxamide 1-oxide dihydrochloride (CM 57755) are thus obtained which, after crystallization in 95% ethanol, melts at 160°–162° C.

EXAMPLE 2

To a solution of 6.4 g of 2-(5-dimethylaminomethylfuran-2-ylmethylthio)ethylamine, 12.7 ml of diisopropylamine in 50 ml of methylene chloride are added, portionwise, at 0°–5° C. and with stirring, 8.7 g of nicotinoyl chloride 1-oxide hydrochloride. The reaction mixture is left for 3 hours at 0°–5° C., then is evaporated to dryness under reduced pressure, the residue is taken up with 40 ml of water and acidified with hydrochloric acid. The acid solution is washed twice with 30 ml of ethyl acetate and is filtered with charcoal and is made clearly basic with concentrated sodium hydroxide. The product is extracted with ethyl acetate, the organic solution is dried over anhydrous sodium sulfate and is evaporated to dryness. The residue is taken up with a small quantity of diethyl ether. After filtration of the crystals and recrystallisation from ethyl acetate, 5.2 g of N-[2-(5-dimethylaminomethylfuran-2-ylmethylthio)ethyl]-3-pyridinecarboxamide 1-oxide, CM 57862 are obtained: m.p. 76° to 78° C.

EXAMPLE 3

To a solution of 1 g of N-[2-(5-dimethylaminomethylfuran-2-ylmethylthio)ethyl]-3-pyridinecarboxamide 1-oxide in 15 ml of ethanol is added a solution of 0.3 g of oxalic acid in 10 ml of ethanol. The salt which precipitates is filtered, dried and crystallized in 10 ml of 95% ethanol. In this way, 1 g of oxalate of N-[2-(5-dimethylaminomethylfuran-2-ylmethylthio)ethyl]-3-pyridinecarboxamide 1-oxide (CM 57874) is obtained; m.p. 105° to 107° C.

EXAMPLE 4

To a solution of 10.2 g of dihydrochloride of N-[2-(5-dimethylaminomethylfuran-2-ylmethylthio)ethyl]-3-pyridinecarboxamide 1-oxide in 15 ml of water is added sodium hydroxide to obtain a clearly basic reaction. The mixture is extracted with ethyl acetate containing 10% ethanol, the organic phase is dried over anhydrous sodium sulfate and is evaporated to dryness. A viscous liquid is thus obtained which crystallizes slowly. The product is triturated in diethyl ether, filtered and dried. After crystallisation from 30 ml of ethyl acetate, 6.8 g of N-[2-(5-dimethylaminomethylfuran-2-yl-methylthio)ethyl]-3-pyridinecarboxamide 1-oxide are obtained, identical to the product of Example 2.

EXAMPLE 5

Tablets having the following composition:

| | |
|---|---|
| CM 57755 | 100 mg |
| lactose | 70 mg |
| potato starch | 40 mg |
| polyvinylpirrolidone | 8 mg |
| magnesium stearate | 2 mg |

The mixture of the active substance with the lactose and potato starch is moistened with a 15% alcohol solution of polyvinylpyrrodidone, the granule formed is passed through a 1 mm sieve, it is mixed with the magnesium stearate and tablets are formed by compression. Weight of a tablet: 220 mg.

EXAMPLE 6

The tablets manufactured as described in Example 5 are coated in known manner by a coating for pills consisting essentially of sugar and talc and the finished pills are polished with beeswax. Weight of a pill: 300 mg.

EXAMPLE 7

Capsules having the following composition:

| | |
|---|---|
| CM 57755 | 200 mg |
| cornstarch | 90 mg |
| talc | 10 mg |

The active ingredient and the excipients are intimately mixed and the mixture thus obtained is introduced into capsules of gelatine of dimension 1. Contents of a capsule: 300 mg.

EXAMPLE 8

Suppositories having the following composition

| CM 57755 | 300 mg |
|---|---|
| mass for suppository (Witespol W 45) | 1450 mg |

The finely pulverized active substance is placed in suspension in the mass for suppositories at 37° C. and the mixture is poured into moulds which were slightly cooled beforehand. Weight of a suppository: 1750 mg.

EXAMPLE 9

Tablets having the following composition:

| CM 57755 | 300 mg |
|---|---|
| microcrystalline cellulose | 100 mg |
| cornstarch | 50 mg |
| polyvinylpyrrolidone | 10 mg |
| magnesium stearate | 5 mg |

The active ingredient is mixed with the three excipients, the mixture obtained is passed through an 0.5 mm sieve, then the lubricating magnesium stearate is added and the mixture is compressed.

Tablets containing 500 mg of CM 57755 are prepared in the same way.

EXAMPLE 10

Capsules having the following composition:

| CM 57755 | 350 mg |
|---|---|
| cornstarch | 140 mg |
| talc | 10 mg |

The active ingredient is intimately mixed with the excipients and the mixture thus obtained is introduced into capsules of gelatine of dimension 0.

Tablets containing 500 mg of CM 57755 are prepared in the same way.

We claim:

1. A compound selected from the group consisting of the N-[2-(5-dimethylaminomethylfuran-2-ylmethylthio)ethyl]-3-pyridinecarboxamide 1-oxide of formula:

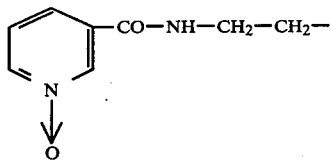

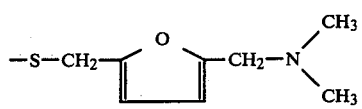

and the pharmaceutically acceptable acid addition salts thereof.

2. The N-[2-(5-dimethylaminomethylfuran-2-ylmethylthio)ethyl]-3-pyridinecarboxamide 1-oxide dihydrochloride.

3. A pharmaceutical composition in dosage unit form having histamine $H_2$ receptor blocking activity comprising from 10 to 1000 mg per dosage unit of an active ingredient as claimed in claims 1 or 2 in admixture with a pharmaceutically acceptable carrier.

4. A pharmaceutical composition as claimed in claim 3, in which the active ingredient is the N-[2-(5-dimethylaminomethylfuran-2-ylmethylthio)ethyl]-3-pyridinecarboxamide 1-oxide dihydrochloride.

* * * * *

UNITED STATES PATENT AND TRADEMARK OFFICE
CERTIFICATE OF CORRECTION

PATENT NO. : 4,474,790  Page 1 of 2
DATED : October 2, 1984
INVENTOR(S) : Dino Nisato; Sergio Boveri It is certified that error appears in the above—identified patent and that said Letters Patent is hereby corrected as shown below:

| | | |
|---|---|---|
| Column 3 | Line 15, | "hydroxide carbonate." should read --hydroxide or carbonate.-- |
| | Line 23, | "product" should read --products-- |
| | Line 40, | "4; 127-221)." should read --4; 217-221).-- |
| | Line 47, | "N-[2[[5-](dimethylamino)" should read --N-[2[[5-[(dimethylamino)-- |
| Column 4 | Line 20, | "inhibits the 50% by" should read --inhibits by 50% the-- |
| | Line 32, | "It activity" should read --Its activity-- |
| Column 5 | Line 15, | "flavouring and" should read --flavouring agent and-- |
| | Line 37, | "Nine nicotinoyl" should read --Nine g of nicotinoyl-- |

UNITED STATES PATENT AND TRADEMARK OFFICE
CERTIFICATE OF CORRECTION

PATENT NO. : 4,474,790

DATED : October 2, 1984

INVENTOR(S) : Dino Nisato; Sergio Boveri

It is certified that error appears in the above—identified patent and that said Letters Patent is hereby corrected as shown below:

Column 5 Line 47, "solution cooled" should read --solution is cooled--

Column 6 Line 1, "filtration of the" should read --filtration from--

Line 46, "polyvinylpyrrodidone" should read --polyvinylpyrrolidone--

Signed and Sealed this

Twelfth Day of November 1985

[SEAL]

Attest:

Attesting Officer

DONALD J. QUIGG

Commissioner of Patents and Trademarks